United States Patent
Remon et al.

(10) Patent No.: US 10,335,371 B2
(45) Date of Patent: Jul. 2, 2019

(54) SOLID PHARMACEUTICAL DOSAGE FORM SUITABLE FOR USE AS DRINKING WATER MEDICATION

(71) Applicants: Universiteit Gent, Ghent (BE); Orotech NV, Temse (BE)

(72) Inventors: Jean-Paul Remon, Melle (BE); Chris Vervaet, Kachtem (BE); Brenda Vermeulen, Kruibeke (BE)

(73) Assignees: Universiteit Gent (BE); Orotech NV (BE)

( * ) Notice: Subject to any disclaimer, the term of this patent is extended or adjusted under 35 U.S.C. 154(b) by 0 days.

(21) Appl. No.: 15/551,636

(22) PCT Filed: Feb. 17, 2016

(86) PCT No.: PCT/EP2016/053323
§ 371 (c)(1),
(2) Date: Aug. 17, 2017

(87) PCT Pub. No.: WO2016/131853
PCT Pub. Date: Aug. 25, 2016

(65) Prior Publication Data
US 2018/0064650 A1 Mar. 8, 2018

(30) Foreign Application Priority Data
Feb. 17, 2015 (EP) .................................... 15155358

(51) Int. Cl.
| | | |
|---|---|---|
| *A61K 31/00* | (2006.01) | |
| *A61K 9/00* | (2006.01) | |
| *A61K 9/16* | (2006.01) | |
| *A23K 10/00* | (2016.01) | |
| *A23K 50/10* | (2016.01) | |
| *A23K 50/75* | (2016.01) | |
| *A23K 50/30* | (2016.01) | |
| *A23K 20/163* | (2016.01) | |
| *A23K 20/195* | (2016.01) | |
| *A23K 20/121* | (2016.01) | |
| *A61K 31/351* | (2006.01) | |
| *A61K 31/505* | (2006.01) | |

(52) U.S. Cl.
CPC ............ *A61K 9/1652* (2013.01); *A23K 10/00* (2016.05); *A23K 20/121* (2016.05); *A23K 20/163* (2016.05); *A23K 20/195* (2016.05); *A23K 50/10* (2016.05); *A23K 50/30* (2016.05); *A23K 50/75* (2016.05); *A61K 9/0095* (2013.01); *A61K 9/1623* (2013.01); *A61K 31/00* (2013.01); *A61K 31/351* (2013.01); *A61K 31/505* (2013.01)

(58) Field of Classification Search
None
See application file for complete search history.

(56) References Cited

U.S. PATENT DOCUMENTS

| | | | | |
|---|---|---|---|---|
| 5,460,823 A | * | 10/1995 | Jensen | A61K 9/14 424/451 |
| 2004/0228919 A1 | | 11/2004 | Houghton et al. | |
| 2005/0003000 A1 | | 1/2005 | Einig et al. | |
| 2009/0326078 A1 | * | 12/2009 | Remon | A61K 9/1623 514/778 |
| 2011/0294864 A1 | * | 12/2011 | Remon | A61K 31/167 514/420 |

FOREIGN PATENT DOCUMENTS

| | | |
|---|---|---|
| EP | 0 671 174 A2 | 3/1995 |
| WO | 03/074031 A1 | 9/2003 |
| WO | 2004/078122 A2 | 9/2004 |
| WO | 2008/000453 A2 | 1/2008 |
| WO | 2008/099068 A2 | 8/2008 |
| WO | 2010/081815 A1 | 7/2010 |
| WO | 2013/147618 A1 | 10/2013 |

OTHER PUBLICATIONS

Emulsifiers with HLB Values (Year: 2018).*
Ibuprofen entry—Merck Index—2013 (Year: 2013).*
Glucidex—SignetChem—2011 (Year: 2011).*
International Search Report pertaining to PCT Application No. PCT/EP2016/053323, filed Feb. 16, 2017, 5 pages.
Written Opinion pertaining to PCT Application No. PCT/EP2016/053323, filed Feb. 16, 2017, 6 pages.
Spears, J.W., Ionophores and Nutrient Digestion and Absorption in Ruminants, The Journal of Nutrition, American Society for Nutrition, vol. 120, No. 6, Jan. 1, 1990, pp. 632-638, USA.

* cited by examiner

*Primary Examiner* — Abigail Vanhorn
(74) *Attorney, Agent, or Firm* — Dinsmore & Shohl LLP

(57) ABSTRACT

The present invention relates to solid pharmaceutical dosage forms suitable for use as drinking water medication. More in particular, the present invention provides solid pharmaceutical dosage forms comprising a pharmaceutically active agent, a non-ionic surfactant having an Hydrophilic Lipophilic Balance (HLB) of at least 8, and a maltodextrin. The present invention also provides the use of such pharmaceutical dosage forms in veterinary medicine, more in particular as drinking water medication; as well as methods for preparing such pharmaceutical dosage forms.

6 Claims, No Drawings

SOLID PHARMACEUTICAL DOSAGE FORM SUITABLE FOR USE AS DRINKING WATER MEDICATION

FIELD OF THE INVENTION

The present invention relates to solid pharmaceutical dosage forms suitable for use as drinking water medication. More in particular, the present invention provides solid pharmaceutical dosage forms comprising a pharmaceutically active agent, a non-ionic surfactant having an Hydrophilic Lipophilic Balance (HLB) of at least 8, and a maltodextrin. The present invention also provides the use of such pharmaceutical dosage forms in veterinary medicine, more in particular as drinking water medication; as well as methods for preparing such pharmaceutical dosage forms.

BACKGROUND TO THE INVENTION

Veterinary drugs can be administered to pigs, poultry and calves individually or as mass medication such as drinking water and feed medication. For the treatment of large groups of animals with antimicrobials and antiparasitic drugs, mass medication is preferred above parenteral administration as large numbers of animals can be medicated at the same time. Besides, other factors such as animal welfare and the avoiding of tissue damage and stress are important advantages.

Immediate therapeutical care for all diseased or endangered animals in the flock and a quick change of drug and/or dose are possible in case of drinking water medication compared to feed medication. Additionally, diseased animals tend to stop eating, while mostly they will continue drinking.

One of the problems frequently observed in feed medication is "carry-over" of the drug, which results in contamination of the unmedicated feed in the silo. This often leads to the disapproval of feed and even animals, when drugs concentrations above the maximal residue levels are found in the slaughterhouses. Another fact is that feed medication is often used prophylactically with the result that veterinary drugs are overused and the development of resistance occurs.

The main disadvantages of drinking water medication are the unprofessional use of medication and preparation of the solution or suspension by the farmer, the fact that drug uptake can vary dramatically in function of the animals and solubility and stability problems often occur in relation to the formulation. The drinking water medication needs to be physically and chemically stable over a sufficient period of time to allow a homogeneous dose administration and consequently an efficient therapy.

An important limitation for an application via drinking water is the low water solubility of many antimicrobials and antiparasitic drugs. Different mechanisms are described to improve water solubility of the drug such as complexation with cyclodextrins, production of self-emulsifying drug delivery systems, the use of phospholipid micro-emulsions and the formulation of solid solutions. However, these technologies cannot be applied for veterinary drug formulations as they are too expensive. Therefore there is a need for alternative preparation methods.

Compounds with a low water solubility are mainly formulated as liquids, such as dissolved in a valuable solvent, or provided as suspensions or emulsions. As a consequence, drugs are often low dosed in the formulation. Hence, and in order to obtain suitable dosing amounts, an important amount of liquid, containing large amounts of non-active ingredients (solvents, water) needs to be transported, which is very inefficient and expensive. Another disadvantage of liquid formulations is that they are often characterised by a limited stability. Therefore, the development of a solid formulation such as powders or granules to be redispersed in water is recommended.

Although solid formulations are known from the prior art, these often have the disadvantage of sedimentation after a certain period of time after application in the drinking water. Hence, a large amount of active ingredient is lost at the bottom of the drinking through.

For example WO2008000453 describes that aqueous slurries were prepared including a drug substance, maltodextrin and a surfactant, after which the mixtures were formulated by spray-drying these slurries. WO03074031 describes that maltodextrin with PEG400 and a drug are formed into solid granules (i.e. not a multiparticulate form).

However, it should be noted that the used maltodextrines in these publications have a low or medium DE (Dextrose Equivalent), i.e. being less than 10 (e.g. Novelose 330 has a DE of 5-7), while we discovered that maltodextrins having a DE of at least 10 are essential in the context of the present invention. As detailed in the examples, we have found that decreasing the DE value, results in an increased particle size of the multiparticulate formulations of the present invention, and thus an increased risk of sedimentation after suspension of the obtained particles.

Hence, we have now developed a novel production process for obtaining spray-dried solid pharmaceutical multiparticulate dosage forms that remain stable in drinking water or delivery systems for a long period of time. The present invention specifically relates to spray-dried pharmaceutical dosage forms, in contrast to freeze-dried pharmaceutical dosage forms such as for example disclosed in US20040228919 or WO2004078122. Evidently, freeze-drying and spray-drying are very different processes and compositions suitable for freezed-drying are not readily suitable for spray-drying. The specific components of the formulations of the present invention are selected such that they render the formulations particularly suitable for spray-drying.

Key to the process of the present invention, and ultimately the new dosage form, is the combination of a non-ionic surfactant having an Hydrophilic Lipophilic Balance (HLB) of at least 8 and a maltodextrin having a DE (Dextrose Equivalent) value of at least 10. Said production process consists of two parts. In a first part, the particle size of the compound is decreased to the low micrometer range (below 10 μm) by wet milling with addition of said non-ionic surfactant, to improve the wettability of the compound. Hence, it is also key to the process that a non-solubilized active ingredient is used, since solubilized active ingredients, such as for example used in WO2010081815, cannot be milled. In the second part, the obtained suspension is spray-dried in the presence of maltodextrin to obtain an easily dispersible powder that remains physically stable during the time of administration via drinking water. As such, the obtained formulation can also be used for administration via proportioners. In proportioners, more concentrated suspensions are prepared and because of the low water solubility of many compounds, the preparation of such concentrated suspensions is difficult. A proportioner takes a small amount of a concentrated drug formulation redispersed in water and introduces it into the drinking water line. A 1% proportioner means that 1% of the concentrated dispersion (e.g. 1 ml) is diluted with 99% of drinking water (e.g. 99 ml)

SUMMARY OF THE INVENTION

In a first aspect, the present invention provides a solid pharmaceutical dosage form comprising:
  a pharmaceutically active ingredient,
  a non-ionic surfactant having an Hydrophilic Lipophilic Balance (HLB) of at least 8, and
  a maltodextrin.

In particular, the present invention provides a spray-dried solid pharmaceutical multiparticulate dosage form comprising:
  a pharmaceutically active non-solubilized ingredient,
  a non-ionic surfactant having an Hydrophilic Lipophilic Balance (HLB) of at least 8, and
  a maltodextrin, having a DE (Dextrose Equivalent) value of at least 10.

In a particular embodiment of said pharmaceutical dosage form, said pharmaceutically active ingredient is a poorly water-soluble active agent, more in particular a pharmaceutically active ingredient selected from the list comprising: antibiotics such as pyrimidine antibacterial chemotherapeutics and macrocylic lactones; anticoccidials; or non-steroidal anti-inflammatory drugs.

In a further embodiment of said pharmaceutical dosage form, said non-ionic surfactant preferably has an HLB of 12 to 17; more preferably an HLB of about 15. More in particular, said non-ionic surfactant is a polysorbate, preferably a polysorbate selected from the list comprising polysorbate 20, polysorbate 40, polysorbate 60 and polysorbate 80; more preferably polysorbate 80.

In another particular embodiment of said pharmaceutical dosage form, said maltodextrin is selected from the list comprising maltodextrin with a Dextrose Equivalent (DE) or 18, maltodextrin with a DE of 14, or maltodextrin with a DE of 9; more in particular maltodextrin with a DE of 18.

In a particular embodiment, the solid pharmaceutical dosage form according to this invention preferably comprises a maltodextrin having a DE of 18, and a non-ionic surfactant having an HLB of about 15.

In another particular embodiment of said pharmaceutical dosage form, said pharmaceutically active ingredient and said non-ionic surfactant are present in a ratio of about 4:1-about 1:3, in the solid pharmaceutical dosage form according to this invention.

In a further aspect, the present invention provides a solid pharmaceutical dosage form according to this invention, for us in veterinary medicine, more in particular for use as drinking water or feed medication in veterinary medicine.

The present invention also provides a method for the preparation of a spray-dried solid pharmaceutical multiparticulate dosage form according to this invention; said method comprising the steps of:
  preparing a suspension comprising said pharmaceutical active ingredient, said non-ionic surfactant and water;
  milling said suspension;
  adding said maltodextrin to said milled suspension; and
  spray-drying said milled suspension In a further aspect, the present invention provides the use of a combination of at least one non-ionic surfactant having an Hydrophilic Lipophilic Balance (HLB) of 8 to 20, at least one maltodextrin, and at least one pharmaceutically active ingredient in the preparation of a solid pharmaceutical dosage form.

In a particular embodiment of said method or use as defined herein, said pharmaceutically active ingredient is a poorly water-soluble active agent, more in particular a pharmaceutically active ingredient selected from the list comprising: antibiotics such as pyrimidine antibacterial chemotherapeutics and macrocylic lactones; anticoccidials; or non-steroidal anti-inflammatory drugs.

In a further embodiment of said method or use as defined herein, said non-ionic surfactant preferably has an HLB of 12 to 17; more preferably an HLB of about 15. More in particular, said non-ionic surfactant is a polysorbate, preferably a polysorbate selected from the list comprising polysorbate 20, polysorbate 40, polysorbate 60 and polysorbate 80; more preferably polysorbate 80.

In another particular embodiment of said method or use as defined herein, said maltodextrin is selected from the list comprising maltodextrin with a Dextrose Equivalent (DE) or 18, maltodextrin with a DE of 14, or maltodextrin with a DE of 9; more in particular maltodextrin with a DE of 18.

In a particular embodiment of said method or use as defined herein, the solid pharmaceutical dosage form according to this invention preferably comprises a maltodextrin having a DE of 18, and a non-ionic surfactant having an HLB of about 15.

In another particular embodiment of said method or use as defined herein, said pharmaceutically active ingredient and said non-ionic surfactant are present in a ratio of about 4:1-about 1:3, in the solid pharmaceutical dosage form according to this invention.

DETAILED DESCRIPTION OF THE INVENTION

As already indicated herein before, in a first aspect, the present invention provides a solid pharmaceutical dosage form comprising:
  a pharmaceutically active ingredient,
  a non-ionic surfactant having an Hydrophilic Lipophilic Balance (HLB) of at least 8, and
  a maltodextrin.

In particular, the present invention provides a spray-dried solid pharmaceutical multiparticulate dosage form comprising:
  a pharmaceutically active non-solubilized ingredient,
  a non-ionic surfactant having an Hydrophilic Lipophilic Balance (HLB) of at least 8, and
  a maltodextrin, having a DE (Dextrose Equivalent) value of at least 10.

In a particular embodiment, the pharmaceutically active ingredient according to the present invention is a poorly water-soluble active agent, more in particular a pharmaceutically active ingredient selected from the list comprising: antibotics such as pyrimidine antibacterial chemotherapeutics (e.g. trimethoprim) and macrocytic lactones (e.g. ivermectine); anticoccidials (e.g. monensin, decoquinate, diclazuril); or non-steroidal anti-inflammatory drugs.

In practice, trimethoprim is always used in combination with one of the following sulfonamide compounds: sulfachloropyridazine (and sodium salt), sulfadiazine (and sodium salt), sulfamethoxazol, sulfadimidine, sulfadimethoxine, sulfaclozine. In the context of the present invention, the sulfonamide component is preferably added at the end of the production process, i.e. after milling and spray-drying the trimethoprim component.

In the context of the present invention, the term 'Hydrophilipic Lipophilic Balance' of as substance is meant to be a measure for the degree to which said substance is hydrophilic or lipophilic, as determined by calculating values for the different regions of the molecule. The higher the HLB of a substance, the more hydrophilic it is. The HLB value of a substance is generally calculated using the Griffin's method, wherein the following formula is applied:

$$HLB = 20 * M_h/M$$

Wherein $M_h$ is the molecular mass of the hydrophilic portion of the molecule and M is the molecular mass of the whole molecule thereby giving a result on a scale of 0 to 20.

Substances having an HLB of at least 10 are hydrophilic, while substances having an HLB less than 10 are only water dispersible or hydrophobic. For example, the polysorbates as mentioned hereinafter are very suitable in the context of the present invention since they have an HLB of at least 8, in particular between 8 and 20, more in particular between 10 and 17, more in particular between 14 and 17, more in particular about 15: Polysorbate 20 (HLB=16.7), Polysorbate 40 (HLB=15.6), Polysorbate 60 (HLB=14.9), Polysorbate 80 (HLB=15.0).

Maltodextrin as used in the current invention is a polysaccharide of aeneral formula I:

$$\text{Formula I}$$

$$\left[ \begin{array}{c} CH_2OH \\ \phantom{xxx} \\ H{-}O{-}\phantom{x}\overset{OH}{\phantom{xxx}}\phantom{x}{-}OH \\ OH \end{array} \right]_n$$

$$\alpha\text{-}1,4$$
$$2 < n < 20$$

Maltodextrins are classified by dextrose equivalent (DE) and have a DE between 3 to 20. The higher the DE value, the shorter the glucose chains. The term 'dextrose equivalent (DE)' is a measure of the amount of reducing sugars present in a sugar product, relative to dextrose (a.k.a glucose), expressed as a percentage on a dry basis. For example, a maltodextrin with a DE of 10 would have 10% of the reducing power of dextrose (which has a DE of 100). In the context of the present invention maltodextrines having a DE of at least 10, more in particular of 14 or 18 are preferred. Most preferred are maltodextrines having a DE of 18.

Hence, in a particular embodiment, the solid pharmaceutical dosage form according to this invention preferably comprises a maltodextrin having a DE of 18, and a non-ionic surfactant having an HLB of about 15.

In a further aspect, the present invention provides a solid pharmaceutical dosage form according to this invention, for use in veterinary medicine, more in particular for use as drinking water or feed medication in veterinary medicine. The dosage form according to this invention was found to solve the problems associated with prior art known dosage forms, and remain stable in drinking water or delivery systems for a long period of time. As such, and in contrast to many prior art known formulations, the obtained formulations can be used for administration via proportioners.

In view of the preferred administration of the dosage form via proportioners, and the desired improvement in resuspension, the solid pharmaceutical dosage form according to this invention is preferably in the form of low-micrometer-sized (e.g. less than 10 µm, preferably less than 5 µm), or nanometer-sized particles, since these small particles are easier to disperse and to remain in suspension for a longer period of time. It was found that such small-sized particles could be obtained using the method according to the present invention.

Hence, in a further aspect, the present invention provides a method for the preparation of a spray-dried solid pharmaceutical dosage form according to this invention; said method comprising the steps of:
preparing a suspension comprising said pharmaceutical active ingredient, said non-ionic surfactant and water;
milling said suspension;
adding said maltodextrin to said milled suspension; and
spray-drying said milled suspension In particular, the present invention provides a method for the preparation of a spray-dried solid pharmaceutical dosage form according to this invention; said method comprising the steps of:
preparing a suspension comprising said pharmaceutical active ingredient, said non-ionic surfactant and water;
milling said suspension;
adding said maltodextrin to said milled suspension; and
spray-drying said milled suspension.

The process according to the present invention is a 2-part process: in the first part of the process, the pharmaceutically active agent and the non-ionic surfactant are added to demineralised water and the suspension is milled, preferably in the presence of zirconium oxide milling beads. In the second part of the process the milled suspension is spray-dried, using maltodextrin as a spray-drying carrier. In addition, it was found that the presence of maltodextrin in the formulations according to this invention, also secures the stability of the formulation after redispersion.

Although the use of zirconium oxide milling beads is preferred within the context of the present invention, any other type of suitable milling beads/balls may be used, as long as they are compatible with the used ingredients, and their use results in a reduction of the particle size of the starting material. Alternative milling beads include for example zirconium silicate beads, steel beads (e.g. chromium steel or cast steel), glass beads, ceramic beads, . . . .

Depending on the actually used pharmaceutically active agent, the concentrations and ratios of pharmaceutically active agent to non-ionic surfactant may be varied, and are preferably between about 4:1 and about 1:3. For example, when using monensin as the active ingredient, preferably a ratio of about 3:1 (MON/polysorbate) is used; when using decoquinate as the active ingredient, preferably a ratio of about 3:1 (DEQ/polysorbate) is used; when using trimethoprim as the active ingredient, preferably a ratio of about 1:2 (TRI/polysorbate) is used.

The time of milling the suspension is dependent on the type of milling beads and used milling device. For example when using small laboratory scale milling devices, a milling time of about 24 h may be needed for obtaining a suitable particle size, while large scale industrial milling devices may only need about 1 to 2 h to obtain the same effect. Regardless of the used milling device and type of milling beads, the milling process is preferably continued until the particle size of the preparation is reduced to about less than 10 µm, preferably about 5 µm or less.

EXAMPLES

Example 1

Preparation of a Monensin Dispersible Powder

A monensin dispersible powder was prepared as follows: in the first part of the process, monensin and polysorbate 80 were added to demineralised water and this suspension was milled in the presence of zirconium oxide milling beads. In the second part of the process, maltodextrin was added as spray-drying carrier and the milled suspension was spray-dried.

An experiment on lab scale was performed to study the effect of the monensin-polysorbate 80 ratio on the particle size of the suspension, the particle size of the spray-dried powder and on the yield of the spray-drying process.

Therefore, 1 g monensin (sodium) and different amounts of polysorbate 80 (Tween® 80) ranging between 0 and 1 g were added to 5 ml of demineralised water together with 30 g of zirconium oxide milling beads (diameter 0.4-0.5 mm) and milling was performed during 24 h on a lab scale machine (Roller-mill, Peira, Beerse). Then, the milling beads were removed from the suspension and an amount of maltodextrin (C*Pharm Dry 01983) was added as spray-drying carrier to obtain a final concentration of 50% (w/w) monensin in the spray-dried powder. The suspension was spray-dried using a Buchi Mini Spray Dryer B-290 (Buchi, Germany) (settings: feed flow=3.5 ml/min, spray-gas flow=536 L/h–volume flow=32.5 m$^3$/h–inlet temperature=120° C.–outlet temperature=±50° C.). Particle size was determined by laser diffraction (Malvern Mastersizer, wet method) and the yield of the spray-drying process was calculated.

From the results shown in Table 1, it can be concluded that the addition of Tween® 80 is required in order to obtain a decrease of the particle size during milling. The formulation milled without addition of Tween® 80 shows a mean particle size (expressed as D(v,0.9)) of 74.51 µm, while in case of addition of Tween® 80, the particle size decreases below 1 µm. When considering the yield of the spray-drying process, it can be seen that an increased amount of Tween® 80 results in a decreased yield. It can be concluded that a monensin-polysorbate ratio nearby 80:20 results in a spray-dried powder with a particle size around 1 µm after redispersion and a good yield (±75%) of the spray-drying process. When spray-drying a formulation consisting of equal amounts of monensin and Tween® 80 (ratio 50:50) no powder but only a sticky material was obtained, indicating the need of using a carrier for the spray-drying process in casu maltodextrins.

TABLE 1

Effect of the monensin - polysorbate 80 (Tween ® 80, TW80) ratio on the particle size (expressed as D(v, 0.9)) of the suspension and the spray-dried powder and on yield of the spray-drying process

| Amount MON/TW80 | Ratio MON:TW80 | D(v, 0.9) (µm) Suspension | D(v, 0.9) (µm) SD powder | Yield (%) |
|---|---|---|---|---|
| 1 g/0 g | 100:0 | 74.51 | | |
| 1 g/0.25 g | 80:20 | 0.64 | 1.012 | 74 |
| 1 g/0.5 g | 67:33 | 0.62 | 0.920 | 6 |
| 1 g/0.75 g | 57:43 | 0.64 | 0.984 | 38 |

D(v, 0.9) (µm) is defined as 90% of the total volume of the distribution lies below this diameter Particle size of the spray-dried powder was determined after redispersion of the powder in water The effect of the final concentration of monensin in the spray-dried powder on the particle size of the spray-dried powder and the yield of the spray-drying process was studied too. Therefore a suspension consisting of 1 g monensin and 0.3 g polysorbate 80 (Tween® 80) in 5 ml demineralised water was milled as described above. After removing the milling beads, different amounts of maltodextrin (C*Pharm Dry 01983) were added as spray-drying carrier to obtain a final concentration of 20, 30, 40 or 50% (w/w) monensin in the spray-dried powder. These suspensions were spray-dried as described above. The yield of the spray-drying process was calculated and the particle size of the spray-dried powder was measured. The results are shown in Table 2.

TABLE 2

Particle size (expressed as D(v, 0.9)) of the spray-dried powder and yield of the spray-drying process for formulations with different concentrations of monensin

| Conc. (%, w/w) monensin in spray-dried powder | D(v, 0.9) (µm) | Yield (%) |
|---|---|---|
| 20% | 0.66 | 62 |
| 30% | 0.74 | 75 |
| 40% | 0.84 | 74 |
| 50% | 5.38 | 63 |

D(v, 0.9) (µm) is defined as 90% of the total volume of the distribution lies below this diameter Particle size of the spray-dried powder was determined after redispersion of the powder in water It can be concluded that formulations with a monensin concentration up to 40% (w/w) have a particle size below 1 µm after redispersion when spray-dried on lab scale, while a formulation with 50% (w/w) monensin results in a particle size above 5 µm. It can be concluded that a final concentration of monensin of 30-40% (w/w) results in a spray-dried powder with a particle size below 1 µm after redispersion and a good yield (±75%) of the spray-drying process.

In a final experiment, the suspension was prepared on an industrial mill (LMZ 10, Netzsch, Germany). Therefore, 40 kg monensin and 12 kg Tween® 80 were added to 148 kg demineralised water. This mixture was milled for 270 min in the presence of zirconium oxide beads (diameter 0.4-0.5 mm). The obtained suspension was spray-dried on industrial scale (Niro P 6.3, Niro, Denmark) (inlet temperature=180° C.–outlet temperature=85° C.). Maltodextrin (C*PharmDry 01983) was added as spray-drying carrier in an amount to obtain a powder containing 40% (w/w) monensin. The particle size of the suspension and the spray-dried powder was determined as described above and the yield of the spray-drying process was calculated. A particle size of ±2.50 µm was reached after 270 min of milling. Spray-drying of the milled suspension resulted in a formulation with a particle size of 5±2 µm after redispersion and the yield of the spray-drying process was above 90% (i.e. 94%).

In addition a redispersion test in hard water (prepared according to guideline EMEA/CVMP/430/03—Revised) was performed. Therefore, an amount of the formulation corresponding with an amount corresponding with the use of a 1% proportioner application was redispersed in hard water and the onset of sedimentation or flotation was observed over a period of 24 h.

It could be concluded that no sedimentation nor flotation was observed within 24 h. This means that the increased particle size of the spray-dried powder compared to the experiments on lab scale has no influence on the redispersion of the powder and its physical stability after dilution. The industrial formulation can be used for at least 24 h after redispersion in drinking water.

Comparison of the Developed Formulation with Commercially Available Products:

The developed drinking water formulation was compared with two commercially available (in New Zealand) products. Rumenox® consists of granules containing 30% monensin and Rumensin® Max is a liquid containing 15% monensin. For each formulation (developed formulation, Rumenox® Rumenox and Rumensin® Max), an amount corresponding to a proportioner of 1% was dispersed in hard water. For both commercially available products, sedimentation was observed after 12 h, while no sedimentation was observed within 24 h for the newly developed formulation.

---

RUMENSIN ® MAX (Elanco - WO2002049609)

Brown gelatinous fluid, which can be used in proportioners, and results in a watery suspension
Concentration: 15% monensin (sodium)
Particle size: D(v, 0.9) = 100 ± 50 µm
Additives:
Alkylpolyglycoside (wetting agent/surfactant)                 5-10%
Gensil antifoam 2030 (mixture) (antifoaming agent)            0.1-1%
Didecyldimethylammoniumbromide 70%                            0.1-1%
Non hazardhous substances                                     64-64.8%
RUMENOX ® (Glenmark Veterinary Limited - New-Zealand)

Granules obtained by dry granulation
Concentration: 30% monensin (sodium)
Particle size: D(v, 0.9) = 220 µm

---

Evaluation of the Effect of Different Maltodextrins

In this part, we have tested the effect of different maltodextrins (i.e. maltodextrins with different DE-values) on particle size and redispersion capacity. Thereto, 1,4 g monensin (sodium) and 0.42 g polysorbate 80 (Tween® 80) were added to 5 ml of demineralised water together with 30 g of zirconium oxide milling beads (diameter 0.4-0.5 mm) and milling was performed during 24 h on a lab scale machine (Roller-mill, Peira, Beerse). Then, the milling beads were removed from the suspension and an amount of maltodextrin (C*Pharm Dry 01983) having a DE-value of 18, 14 or 9 was added as spray-drying carrier to obtain a final concentration of 40 (w/w) monensin in the spray-dried powder. The suspension was spray-dried using a Buchi Mini Spray Dryer B-290 (Buchi, Germany) (settings: feed flow=3.5 ml/min, spray-gas flow=536 L/h–volume flow=32.5 m$^3$/h–inlet temperature=120° C.–outlet temperature=±50° C.). Additionally, a milled suspension without addition of maltodextrin was spray-dried too.

Particle size was determined by laser diffraction (Malvern Mastersizer, wet method) and the yield of the spray-drying process was calculated. It can be concluded that maltodextrins with different DE-values can be used, however, the particle size of the powder obtained after spray-drying increases if the DE-value decreases. It can also be seen that the yield of the spray-drying process decreases in relation with a decreased DE-value. Spray-drying without addition of maltodextrin as carrier is not designated because of the very low yield that is obtained.

In addition, a redispersion test in hard water (prepared according to guideline EMEA/CVMP/430/03—Revised) was performed. Therefore, an amount of each formulation corresponding with the use of a 1% proportioner application was redispersed in hard water and the onset of sedimentation or flotation was observed over a period of 24 h. Despite an increase in particle size when using other maltodextrins, no sedimentation nor flotation was observed within 24 h after redispersion.

Evaluation of the Effect of Different Surfactants

In this part, we have tested the effect of different surfactants (i.e. surfactants with different HLB values) on particle size and redispersion capacity. Thereto, 1.4 g monensin (sodium) and 0.42 g of different surfactants (Sodiumlaurylsulphate (SLS), Lutrol® F68=Poloxamer® 188, Cremophor® A25, Tween® 20, Tween® 60, Tween® 85, Span® 60, Span® 80, Arlacel® 83 and no surfactant) were added to 5 ml of demineralised water together with 30 g of zirconium oxide milling beads (diameter 0.4-0.5 mm) and milling was performed during 24 h on a lab scale machine (Roller-mill, Peira, Beerse). Then, the milling beads were removed from the suspension and an amount of maltodextrin (C*Pharm Dry 01983) having a DE-value of 18 was added as spray-drying carrier to obtain a final concentration of 40% (w/w) monensin in the spray-dried powder.

The suspension was spray-dried using a Buchi Mini Spray Dryer B-290 (Buchi, Germany) (settings: feed flow=3.5 ml/min, spray-gas flow=536 L/h–volume flow=32.5 m$^3$/h–inlet temperature=120° C.–outlet temperature=±50° C.). Particle size was determined by laser diffraction (Malvern Mastersizer, wet method) and the yield of the spray-drying process was calculated. When considering the surfactants with a HLB-value above 10, it can be seen that an increased particle size varying between 4 and 13 µm is obtained. A good yield (60-74%) is obtained for the different surfactant with exception for Lutrol® F68/Poloxamer 188 (11%). No particle size reduction is obtained after milling in the presence of surfactants with an HLB-value below 10 and the obtained suspensions could not be spray-dried due to an increased viscosity. Milling of a formulation with Tween® 85 (HLB=11.0) resulted in a partial particle size reduction (63 µm) and a yield of 26% was obtained after spray-drying this suspension.

In addition a redispersion test in hard water (prepared according to guideline EMEA/CVMP/430/03—Revised) was performed. Therefore, an amount of the formulation corresponding with the use of a 1% proportioner application was redispersed in hard water and the onset of sedimentation or flotation was observed over a period of 24 h. Good redispersible spray-dried powders are obtained when surfactants with an HLB-value between 14 and 18 are used. If surfactants with a higher HLB-value (SLS, Lutrol® F68) are used, sedimentation or flotation occurred. Redispersing the spray-dried formulation with Tween® 85 resulted in sedimentation within 12 h. An overview of the results is shown in table 3.

TABLE 3

Particle size (expressed as D(v, 0.9)), yield and redispersion capacity of the spray-dried powders for monensin formulations using different surfactants

| Surfactant | HLB | D(v, 0.9) (µm) Suspension | D(v, 0.9) (µm) SD powder | Yield (%) | Redispersion |
|---|---|---|---|---|---|
| SLS | 40 | 0.61 | 0.63 | 74 | sedimentation within 6 h |
| Lutrol ® F68 | >24 | 1.50 | 11.13 | 11 | flotation within 3 h |
| Cremophor ® A25 | 15-17 | 0.64 | 3.43 | 60 | no sediment./flotat. after 24 h |

TABLE 3-continued

Particle size (expressed as D(v, 0.9)), yield and redispersion capacity of the spray-dried powders for monensin formulations using different surfactants

| Surfactant | HLB | D(v, 0.9) (μm) Suspension | D(v, 0.9) (μm) SD powder | Yield (%) | Redispersion |
|---|---|---|---|---|---|
| Tween ® 20 | 16.7 | 0.63 | 5.88 | 69 | no sediment./flotat. after 24 h |
| Tween ® 80 | 15.0 | 0.60 | 7.01 | 74 | no sediment./flotat. after 24 h |
| Tween ® 60 | 14.9 | 0.57 | 5.67 | 70 | no sediment./flotat. after 24 h |
| Tween ® 85 | 11.0 | 63.14 | 24.08 | 26 | sedimentation within 12 h |
| Span ® 60 | 4.7 | 219.51 | n.d. | n.d. | n.d. |
| Span ® 80 | 4.3 | 158.19 | n.d. | n.d. | n.d. |
| Arlacer ® 83 | 3.7 | 216.56 | n.d. | n.d. | n.d. |
| No surfactant | — | 203.20 | n.d. | n.d | n.d. |

D(v, 0.9) (μm) is defined as 90% of the total volume of the distribution lies below this diameter

Example 2

Preparation of a Trimethoprim Dispersible Powder

A trimethoprim dispersible powder was prepared as follows: in the first part of the process, trimethoprim and polysorbate 80 were added to demineralised water and this suspension was milled in the presence of zirconium oxide milling beads. In the second part of the process, maltodextrin was added as spray-drying carrier and the milled suspension was spray-dried.

The suspension was prepared by wet milling using a semi-industrial scale mill (LME 4, Netzsch, Germany). Therefore, 0.25 kg trimethoprim and 0.3 kg Tween® 80 were added to 5 L of demineralised water and this mixture was milled during 120 min in the presence of zirconium oxide beads (diameter 1.2-1.5 mm). Larger milling beads were required as no particle size reduction was obtained when using beads with a diameter of 0.4-0.5 mm. The obtained suspension was spray-dried on a semi-industrial scale spray-drier (Niro mobile minor, Niro, Denmark) (settings: pump=40.1 ml/min, pressure=1.5 bar, inlet temperature=150° C.–outlet temperature=±65° C.). Maltodextrin (C*Pharm Dry 01983) was added as spray-drying carrier in an amount to obtain a powder containing 20% (w/w) trimethoprim.

The particle size of the suspension and the spray-dried powder was determined as described above and the yield of the spray-drying process was calculated. A particle size of 217 μm was measured before milling, while a value of 4 μm was obtained after 120 min of milling. The particle size of the spray-dried powder measured after redispersion was ±6.5 μm and the yield of the spray-drying process was 73%.

The redispersion of the formulation in hard water (prepared according to the guideline mentioned above) was studied. In practice, trimethoprim is always used in combination with a sulphonamide compound (s.a. sulfadiazine, sulfachloropyridazine, sulphamethoxazole, . . . ) in a ratio of 1/5. Therefore an amount of the spray-dried formulation containing 20% trimethoprim was mixed with an equal amount of sodium sulfadiazine to obtain a final concentration of 10 trimethoprim and 50% sodiumsulfadiazine. Different amounts of this mixture corresponding with the use of a 10%, 5%, 2.5% and 1% proportioner were redispersed in hard water and the onset of sedimentation and flotation was observed over a period of 24 h.

From the obtained results it can be concluded that no sedimentation nor flotation was observed within 24 h after redispersion with exception of the test where an amount corresponding with the use of a 1% proportioner was added. In that specific case sedimentation was observed 12 h after redispersion of the mixture in hard water.

Comparison with Commercially Available Products:

The developed drinking water formulation was compared with three products available on the Belgian market: Cosumix® Plus (10% sodium sulfachloropyridazine and 2% trimethoprim) powder for drinking water administration that needs to be replaced every 24 h. Trimazin® 30 (25% sodium sulfadiazine and 5% trimethoprim) is also a powder for drinking water medication but it is difficult to redisperse. As indicated on the specific product characteristics (SPC), the powder needs to be dissolved in a small volume of warm water (50-55° C.) and then mixed for 5 min using a mixing device. Thereafter this mixture needs to be added to the rest of the drinking water and the medicated drinking water must be consumed within 4 hours. This operation is performed twice daily. Emdotrim® 60% (50% sodium sulfadiazine and 10 trimethoprim) is a powder that needs to be wetted with a small amount of drinking water and this viscous mixture must be added to the rest of the drinking water. The medicated drinking water has to be consumed within 4 hours. It is mentioned on the SPC that the solubility cannot be guaranteed in case of using a proportioner.

COSUMIX ® PLUS (VMD)

Concentration: 2% trimethoprim + 10% sodiumsulfachloropyridazine
Particle size: D(v, 0.9) = 50 ± 20 μm
Additives: sodiumlaurylsulfate, PEG 6000, sucrose
TRIMAZIN ® 30% (Kela)

Concentration: 5% trimethoprim + 25% sodiumsulfadiazine
Particle size: D(v, 0.9) = 240 μm
Additives: lactose monohydrate
EMDOTRIM ® 60 (Emdoka/Ecuphar)

Concentration: 10% trimethoprim + 50% sodiumsulfadiazine
Particle size: D(v, 0.9) = 230 μm
Additives: anhydric colloidal silica, lactose An amount of formulation corresponding with the use of a 10%, 5% and 2.5% proportioner was used for each of the commercial products and for the developed formulation. It was not possible to redisperse at these concentrations for Trimazin® 30% and Emdotrim® 60%. Sedimentation was formed immediately on the bottom of the recipient, and after 4 h, these formulations were partially floating on top of the water due to an insufficient wetting of the active compound. Cosumix® Plus could be quite easily redispersed in the drinking water but after 12 h, sedimentation was observed for all the proportioner concentrations used. The developed formulation allowed redispersion for 24 h without sedimentation or flotation.

From these tests it can be concluded that Trimazin® 30% and Emdotrim® 60% cannot be used in proportioners. Cosumix® Plus can be used in a proportioner but the drinking water needs to be consumed within 12 h, while for our formulation there are no limitations. Another important advantage for our formulation is the fact that the newly developed formulation contains 60% of active compound (after mixing with the sulphonamide) which is five times more concentrated than Cosumix® Plus.

Example 3

Preparation of a Decoquinate Dispersible Powder

A decoquinate dispersible powder was prepared as follows: in the first part of the process, decoquinate and polysorbate 80 were added to demineralised water and this suspension was milled in the presence of zirconium oxide milling beads. In the second part of the process, maltodextrin was added as spray-drying carrier and the milled suspension was spray-dried.

For the preparation of the formulation, 1 g decoquinate and 0.3 g polysorbate 80 (Tween® 80) were added together with 30 g of zirconium oxide milling beads (diameter 0.4-0.5 mm) to 5 ml of demineralised water and milling was performed during 24 h on a lab scale machine (Roller-mill, Peira, Beerse). The milling beads were removed from the suspension and an amount of maltodextrin (C*Pharm Dry 01983) was added as spray-drying carrier to obtain a final concentration of 20% (w/w) decoquinate in the spray-dried powder. The suspension was spray-dried on the Niro Mobile Minor (Niro, Denmark) (settings: pump=40.1 ml/min, pressure=1.5 bar, inlet temperature=180° C.–outlet temperature=±70° C.). The particle size of the suspension and the spray-dried powder was determined as described above and the yield of the spray-drying process was calculated.

After 24 h of milling, a particle size of ±600 nm was obtained and after redispersing the spray-dried powder a particle size between 500 and 600 nm was measured. The yield of the spray-drying process was ±60%.

The dispersion of the formulation in hard water (prepared according to the guideline mentioned above) was studied. Different amounts of formulation corresponding with the use of a 10%, 5%, 2.5% and 1% proportioner were dispersed in hard water and the onset of sedimentation or flotation was observed over a period of 24 h. From the obtained results it can be concluded that no sedimentation nor flotation was observed within 24 h after dispersion.

Evaluation of the Effect of Different Maltodextrins:

In this part, we have tested the effect of different maltodextrins (i.e. maltodextrins with different DE-values) on particle size and redispersion capacity. Thereto, 1.0 g decoquinate and 0.3 g polysorbate 80 (Tween® 80) were added to 5 ml of demineralised water together with 30 g of zirconium oxide milling beads (diameter 0.4-0.5 mm) and milling was performed during 24 h on a lab scale machine (Roller-mill, Peira, Beerse). Then, the milling beads were removed from the suspension and an amount of maltodextrin (C*Pharm Dry 01983) having a DE-value of 18, 14 or 9 was added as spray-drying carrier to obtain a final concentration of 20% (w/w) decoquinate in the spray-dried powder.

The suspension was spray-dried using a Buchi Mini Spray Dryer B-290 (Buchi, Germany) (settings: feed flow=3.5 ml/min, spray-gas flow=536 L/h–volume flow=32.5 m³/h–inlet temperature=120° C.–outlet temperature=±50° C.). Particle size was determined by laser diffraction (Malvern Mastersizer, wet method) and the yield of the spray-drying process was calculated.

It can be concluded that maltodextrins with different DE-values can be used, to obtain a powder with similar particle size and a similar yield of the spray-drying process. In addition a redispersion test in hard water (prepared according to guideline EMEA/CVMP/430/03—Revised) was performed. Therefore, an amount of each formulation corresponding with the use of a 1% proportioner application was redispersed in hard water and the onset of sedimentation or flotation was observed over a period of 24 h. No sedimentation nor flotation were observed within 24 h after redispersion for the different formulations.

Evaluation of the Effect of Different Surfactants:

In this part, we have tested the effect of different surfactants (i.e. surfactants with different HLB values) on particle size and redispersion capacity. Thereto, 1.0 g decoquinate and 0.3 g of different surfactants (Sodiumlaurylsulphate (SLS), Lutrol® F68=Poloxamer® 188, Cremophor® A25, Tween® 20, Tween® 60, Tween® 85, Span® 60, Arlacel® 83 and no surfactant) were added to 5 ml of demineralised water together with 30 g of zirconium oxide milling beads (diameter 0.4-0.5 mm) and milling was performed during 24 h on a lab scale machine (Roller-mill, Peira, Beerse). Then, the milling beads were removed from the suspension and an amount of maltodextrin (C*Pharm Dry 01983) having a DE-value of 18 was added as spray-drying carrier to obtain a final concentration of 20% (w/w) decoquinate in the spray-dried powder.

The suspension was spray-dried using a Buchi Mini Spray Dryer B-290 (Buchi, Germany) (settings: feed flow=3.5 ml/min, spray-gas flow=536 L/h–volume flow=32.5 m³/h–inlet temperature=120° C.–outlet temperature=±50° C.). Particle size was determined by laser diffraction (Malvern Mastersizer, wet method) and the yield of the spray-drying process was calculated. When considering the surfactants with a HLB-value above 10, it can be seen that an increased particle size varying between 0.5 and 4 µm is obtained. A good yield (60-74%) is obtained after spray-drying for formulations with the different surfactants. A partial particle size reduction is obtained after milling in the presence of surfactants with an HLB-value below 10. The obtained suspensions are not be spray-dried due to an increased viscosity.

In addition, a redispersion test in hard water (prepared according to guideline EMEA/CVMP/430/03—Revised) was performed. Therefore, an amount of the formulation corresponding with the use of a 1 or 2.5% proportioner application was redispersed in hard water and the onset of sedimentation or flotation was observed over a period of 24 h. For a 2.5 proportioner, good redispersible spray-dried powders are obtained when surfactants with an HLB-value between 14 and 18 are used. Sedimentation was observed for a 1% proportioner within 12 h after redispersion for the same surfactants with exception of Tween® 80 where no sedimentation nor flotation was observed within 24 h. When using surfactants with a higher HLB-value, sedimentation and/or flotation occurred for both proportioner concentrations within 4 h (for SLS and Lutrol® F68). When using a surfactant with a lower HLB (Tween® 85, HLB=11.0), no sedimentation/flotation was observed for a 2.5% proportioner, while sedimentation was observed within 4 h for a 1% proportioner. An overview of the results is shown in table 4.

TABLE 4

Particle size (expressed as D(v, 0.9)), yield and redispersion capacity of the spray-dried powders for monensin formulations using different surfactants

| Surfactant | HLB | D(v, 0.9) (μm) Suspension | D(v, 0.9) (μm) SD powder | Yield (%) | Redispersion |
|---|---|---|---|---|---|
| SLS | 40 | 0.71 | 1.80 | 75 | sed. + flot. after 4 h Dos 2.5 + 1% |
| Lutrol ® F68 | >24 | 13.54 | 3.45 | 46 | sed. + flot. after 4 h Dos 2.5 + 1% |
| Cremophor ® A25 | 15-17 | 0.95 | 0.63 | 43 | sed. after 24 h Dos 2.5 + 1% |
| Tween ® 20 | 16.7 | 0.60 | 0.50 | 51 | no sed./flot. after 24 h Dos 2.5% |
|  |  |  |  |  | sedim. after 24 h Dos 1% |
| Tween ® 80 | 15.0 | 0.62 | 0.62 | 69 | no sed./flot. after 24 h Dos 2.5% |
|  |  |  |  |  | no sed./flot. after 24 h Dos 1% |
| Tween ® 60 | 14.9 | 1.06 | 0.53 | 59 | no sed./flot. after 24 h Dos 2.5% |
|  |  |  |  |  | sedim. after 24 h Dos 1% |
| Tween ® 85 | 11.0 | 1.26 | 0.82 | 63 | no sed./flot. after 24 h Dos 2.5% |
|  |  |  |  |  | sedim. after 4 h Dos 1% |
| Span ® 60 | 4.7 | 14.43 | n.d. | n.d. | n.d. |
| Arlacel ® 83 | 3.7 | 59.58 | n.d. | n.d. | n.d. |
| No surfactant | — |  | n.d. | n.d | n.d. |

D(v, 0.9) (μm) is defined as 90% of the total volume of the distribution lies below this diameter Example 4

Preparation of a Diclazuril Dispersible Powder

A diclazuril dispersible powder was prepared as follows: in the first part of the process, diclazuril and polysorbate 80 were added to demineralised water and this suspension was milled in the presence of zirconium oxide milling beads. In the second part of the process, maltodextrin was added as spray-drying carrier and the milled suspension was spray-dried.

For the preparation of the formulation, 0.2 g diclazuril and 0.3 g polysorbate 80 (Tween® 80) were added together with 30 g of zirconium oxide milling beads (diameter 1.0 mm) to 5 ml demineralised water and milling was performed during 24 h on a lab scale machine (Roller mill, Peira, Beerse). The milling beads were removed from the suspension and an amount of maltodextrin (C*Pharm Dry 01983) was added as spray-drying carrier to obtain a final concentration of 2% (w/w) diclazuril in the spray-dried powder. The suspension was spray-dried using a Buchi Mini Spray Dryer B 290 (Buchi, Germany) (settings: feed flow=3.5 ml/min–spray gas flow=536 L/h–volume flow=32.5 m$^3$/h–inlet temperature=170° C.–outlet temperature=±65° C.). Particle size was determined by laser diffraction (Malvern Mastersizer, wet method) and the yield of the spray-drying process was calculated.

After 24 h of milling, a particle size of 600 nm was obtained and after redispersing the spray-dried powder a particle size between 2 and 3 μm was measured. The yield of the spray-drying process was ±50%.

The dispersion of the formulation in hard water (prepared according to the guideline mentioned above) was studied. An amount of spray-dried formulation corresponding with the use of a 1% proportioner was dispersed in hard water and the onset of sedimentation or flotation was observed over a period of 24 h. From the obtained results it can be concluded that no sedimentation nor flotation was observed within 24 h after dispersion.

The invention claimed is:

1. A method for the preparation of a spray-dried solid pharmaceutical multiparticulate dosage form, the method comprising:
    preparing a suspension comprising a pharmaceutical non-solubilized active ingredient, a non-ionic surfactant having an Hydrophilic Lipophilic Balance (HLB) of at least 8 and water;
    milling the suspension;
    adding a maltodextrin to the milled suspension; and
    spray-drying the milled suspension.

2. The method according to claim 1, wherein:
    the non-ionic surfactant has an HLB of 8 to 20; and
    the pharmaceutical non-solubilized active ingredient is selected from the group consisting of antibiotics, anti-coccidials, and non-steroidal anti-inflammatory drugs.

3. The method according to claim 1, wherein the pharmaceutical non-solubilized active ingredient is a poorly water-soluble active agent.

4. The method according to claim 1, wherein the pharmaceutical non-solubilized active ingredient is selected from the group consisting of pyrimidine antibacterial chemotherapeutics, macrocylic lactones, anticoccidials, and non-steroidal anti-inflammatory drugs.

5. The method according to claim 1, wherein the non-ionic surfactant is a polysorbate selected from the group consisting of polysorbate 20, polysorbate 40, polysorbate 60, and polysorbate 80.

6. The method according to claim 1, wherein the maltodextrin is selected from the group consisting of maltodextrin with a Dextrose Equivalent (DE) of 9, maltodextrin with a DE of 14, and maltodextrin with a DE of 18.

* * * * *

UNITED STATES PATENT AND TRADEMARK OFFICE
CERTIFICATE OF CORRECTION

PATENT NO. : 10,335,371 B2
APPLICATION NO. : 15/551636
DATED : July 2, 2019
INVENTOR(S) : Jean-Paul Remon, Chris Vervaet and Brenda Vermeulen It is certified that error appears in the above-identified patent and that said Letters Patent is hereby corrected as shown below:

In the Specification

In Column 4, Line 54, delete "macrocytic" and insert --macrocylic--, therefor.

In Column 5, Line 22, delete "aeneral" and insert --general--, therefor.

In Column 9, Line 2, after "Rumenox®", delete "Rumenox".

In Column 9, Line 26, delete "1,4 g" and insert --1.4 g--, therefor.

In Column 9, Line 35, after "40", insert --%--.

In Column 11, Line 59, after "10", insert --%--.

In Column 12, Line 25, after "30", insert --%--.

In Column 12, Line 36, after "10", insert --%--.

In Column 14, Line 54, after "2.5", insert --%--.

Signed and Sealed this
Tenth Day of March, 2020

Andrei Iancu
*Director of the United States Patent and Trademark Office*